(12) United States Patent
Deckelbaum et al.

(10) Patent No.: US 8,633,253 B2
(45) Date of Patent: *Jan. 21, 2014

(54) OMEGA-3 DIGLYCERIDE EMULSIONS

(71) Applicants: Richard J. Deckelbaum, Hastings on Hudson, NY (US); Yvon Carpentier, Brussels (BE)

(72) Inventors: Richard J. Deckelbaum, Hastings on Hudson, NY (US); Yvon Carpentier, Brussels (BE)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/953,718

(22) Filed: Jul. 29, 2013

(65) Prior Publication Data

US 2013/0315968 A1 Nov. 28, 2013

Related U.S. Application Data

(60) Continuation of application No. 13/783,779, filed on Mar. 4, 2013, which is a division of application No. 12/441,795, filed as application No. PCT/US2007/020364 on Sep. 19, 2007, now Pat. No. 8,410,181.

(60) Provisional application No. 60/845,518, filed on Sep. 19, 2006.

(51) Int. Cl.
*B01F 3/00* (2006.01)

(52) U.S. Cl.
USPC .............................................................. 516/9

(58) Field of Classification Search
USPC .............................................................. 516/9
See application file for complete search history.

(56) References Cited

U.S. PATENT DOCUMENTS

| 5,160,759 A * | 11/1992 | Nomura et al. ............... 426/602 |
| 2003/0144356 A1 * | 7/2003 | Goodale ....................... 514/560 |
| 2003/0149118 A1 | 8/2003 | Akashe et al. |

* cited by examiner

*Primary Examiner* — Daniel Sullivan
*Assistant Examiner* — Trevor Love
(74) *Attorney, Agent, or Firm* — Evans & Molinelli PLLC; Judith Evans

(57) ABSTRACT

The present invention relates to omega-3 diglyceride emulsions characterized in that the lipid phase comprises at least about 40 wt.-% of diglycerides. Preferably about 70 wt.-% of the acyl-groups of said diglycerides, are eicoapentaenoic acid (EPA) groups and/or docasahexaenoic (DHA) groups. The invention further relates to methods of treatment using the omega-3 diglyceride emulsions.

9 Claims, No Drawings

OMEGA-3 DIGLYCERIDE EMULSIONS

CROSS-REFERENCE TO RELATED APPLICATIONS

This application is a continuation application of U.S. application Ser. No. 13/783,779, filed Mar. 4, 2013, which is a divisional application of U.S. application Ser. No. 12/441,795, filed Dec. 8, 2009, now U.S. Pat. No. 8,410,181, which claims priority from International Patent Application No. PCT/US07/020,364, filed Sep. 19, 2007, which claims priority from U.S. Provisional Application Ser. No. 60/845,518 filed Sep. 19, 2006. The contents of which are hereby incorporated by reference in their entirety.

INTRODUCTION

The present invention relates to omega-3 diglyceride emulsions characterized in that the lipid phase comprises at least about 40 wt.-% of diglycerides. Preferably about 70 wt.-% of the acyl-groups of said diglycerides, are eicosapentaenoic acid (EPA) groups and/or docosahexaenoic (DHA) groups. The invention further relates to methods of treatment using the omega-3 diglyceride emulsions.

BACKGROUND OF THE INVENTION

Typically, post-operative and post-traumatic conditions as well as severe septic episodes are characterized by a substantial stimulation of the immune system ischemia reperfusion syndrome, and tendency for thrombosis formation. The immune response is activated by the release of pro-inflammatory cytokines (e.g., tumor necrosis factor and interleukins) which, at high levels, may cause severe tissue damage.

In such clinical conditions, it is of particular importance to provide exogenous lipids that are hydrolyzed and eliminated faster than endogenous lipids (to avoid excessive increases of plasma triglyceride concentration). These lipids supply fatty acids omega-3 fatty acids) capable of reducing cytokine production as well as cytokine toxicity on tissues. Free fatty acids may not be directly administered through the diet or by other parenteral means because they behave as detergents and have toxic side effects. Thus, fatty acids are administered via lipid glycerides such as triglycerides. The fatty acids are released and used after the lipids are catabolized in the body via lipolysis. This effect is obtained when fatty acids are cleaved from the lipid molecules and incorporated (in free form or as components of phospholipids) in cell membranes where they influence membrane structure and cell function, serve as secondary messengers (thus affecting regulation of cell metabolism), influence the regulation of nuclear transcription factors, and are precursors of eicosanoids. Thus, it is desirable that this process take place as quickly as possible.

The human body is capable of synthesizing certain types of fatty acids. However, omega-3 and omega-6 are designated as "essential" fatty acids because they cannot be produced by the human body and must be obtained through other sources. For example, fish oils from cold-water fish have high omega-3 polyunsaturated fatty acids content with lower omega-6 fatty acid content. Most vegetable oils (i.e., soybean and safflower) have high omega-6 polyunsaturated fatty acids (most in the form of 18:2 ($\Delta^{9, 12}$)-linoleic acid) content but low omega-3 (predominantly 18:3 ($\Delta^{9, 12, 15}$)-α-linolenic acid) content.

Essential fatty acids may be obtained through diet or other enteral or parenteral administration. However, the rate of EPA and DHA omega-3 fatty acid enrichment following oral supplementation varies substantially between different tissues and is particularly low in some regions of the brain and in the retina especially when given as the essential fatty acid precursor, α-linolenic acid. Further, human consumption of omega-3 fatty acids has decreased over the past thirty years, while consumption of omega-6 fatty acids has increased, especially in Western populations.

U.S. Application Ser. No. 11/558,568, incorporated herein by reference in its entirety, refers to methods of limiting cell death resulting from hypoxia-ischemia comprising, administering an omega-3 lipid-based emulsion after a hypoxia-ischemia insult. The omega-3 lipid-based emulsion preferably comprises at least 20% omega-3 oil, by weight, and wherein the omega-3 oil comprises at least 20% omega-3 triglycerides and/or diglycerides, and wherein fatty acids of the omega-3 triglyceride and/or diglycerides comprise at least 40% EPA and/or DHA. The application also refers to novel fish-oil compositions for administration after an ischemic insult to limit cell death in the organ that underwent an ischemic event.

Cao et al., "Chronic administration of ethyl docosahexaenoate decreases mortality and cerebral edema in ischemic gerbils", Life Sci. 2005 Nov. 19; 78(1):74-81 alleges that dietary docosahexaenoic acid (DHA) intake can decrease the level of membrane arachidonic acid (AA), which is liberated during cerebral ischemia and implicated in the pathogenesis of brain damage. Cao investigated the effects of chronic ethyl docosahexaenoate (E-DHA) administration on mortality and cerebral edema induced by transient forebrain ischemia in gerbils.

GB 2388026, incorporated herein by reference in its entirety, refers to use n-3 polyunsaturated fatty acids EPA and/or DHA in the preparation of an oral medicament for preventing cerebral damage in patients having symptoms of atherosclerosis of arteries supplying the brain.

Strokin M, Neuroscience. 2006 Jun. 30; 140(2):547-53, incorporated herein by reference in its entirety, investigated the role of docosahexaenoic acid (22:6n-3) in brain phospholipids for neuronal survival.

SUMMARY OF THE INVENTION

The present invention provides a pharmaceutical composition comprising: an omega-3 diglyceride emulsion suitable for administration to a patient; and a pharmaceutically acceptable carrier, wherein the emulsion has a lipid phase of at least about 40 wt.-% of omega-3 diglycerides, and at least about 70 wt.-% of the acyl-groups of the diglycerides comprise EPA, DHA or a mixture thereof.

The present invention also provides a method for preventing organ death or injury comprising: administering to a patient a therapeutically effective amount of a pharmaceutical composition which comprise an omega-3 diglyceride emulsion suitable for administration to a patient; and a pharmaceutically acceptable carrier, wherein the emulsion comprises at least about 40 wt.-% of omega-3 diglycerides.

The present invention further provides a method for reducing adverse cytokine production comprising administering to a patient in need thereof a therapeutically effective amount of a pharmaceutical composition comprising: an omega-3 diglyceride emulsion suitable for administration to a patient; and a pharmaceutically acceptable carrier, wherein the emulsion comprises at least about 40 wt.-% of omega-3 diglycerides.

The present invention further provides a method for reducing cell death or damage resulting from hypoxia-ischemia comprising administering to a patient in need thereof a therapeutically effective amount of a pharmaceutical composition comprising: an omega-3 diglyceride emulsion suitable for administration to a patient; and a pharmaceutically acceptable carrier, wherein the emulsion comprises at least about 40 wt.-% of omega-3 diglycerides.

DETAILED DESCRIPTION OF THE INVENTION

Lipid generally refers to a group of natural substances which are soluble in hydrocarbon and insoluble in water. Lipids include any fat-soluble (hydrophobic) naturally-occurring molecules. The term is more specifically used to refer to fatty-acids and their derivatives (including tri-, di-, and monoglycerides and phospholipids) as well as other fat-soluble sterol-containing metabolites such as cholesterol.

Lipids serve many functions in living organisms including nutrients, energy storage, structural components of cell membranes, and important signaling molecules. Although the term lipid is sometimes used as a synonym for fat, it is in fact a subgroup of lipids called triglycerides and should not be confused with the term fatty acid.

Chemically, fatty acids can be described as long-chain monocarboxylic acids the saturated examples of which have a general structure of $CH_3(CH_2)_nCOOH$. The length of the carbon chain usually ranges from 12 to 24, always with an even number of carbon atoms. When the carbon chain contains no double bonds, it is a saturated chain. If it contains one or more such bonds, it is unsaturated. The presence of double bonds reduces the melting point of fatty acids. Furthermore, unsaturated fatty acids can occur either in cis or trans geometric isomers. In a vast majority of naturally occurring fatty acids, the double bonds are in the cis-configuration.

Polyunsaturated fatty acids (PUFA) include omega-6 (also known as ω-6 or n-6) and omega-3 (also known as ω-3 or n-3) polyunsaturated fatty acids. The designation as omega-3 or omega-6 is based on the fatty acid's structure, namely the distance of the first unsaturated bond from the methyl (omega) end of the fatty acid molecule. Omega-3 polyunsaturated fatty acids mainly include cis-20:5($\Delta^{5,8,11,14,17}$)-eicosapentaenoic acid (EPA); cis-22:5($\Delta^{7,10,13,16,19}$)-docosapentaenoic acid (DPA); cis-22:6($\Delta^{4,7,10,13,16,19}$)-docosahexaenoic acid (DHA); and cis-18:3($\Delta^{3,6,9}$)-α-linoleic acid. Omega-6 polyunsaturated fatty acids mainly include cis-18:2($\Delta^{9,12}$)-linoleic acid and cis-20:4($\Delta^{5,8,11,14}$)-arachidonic acid.

Glycerol is a chemical compound with the formula $HOCH_2CH(OH)CH2OH$. Glycerides are lipids possessing a glycerol (a crude name for which is propan-1,2,3-triol) core structure with one or more fatty acyl groups, which are fatty acid-derived chains attached to the glycerol backbone by ester linkages.

A diglyceride ("DG"), also known as a diacylglycerol, is a glyceride consisting of two fatty acid chains covalently bonded to a glycerol molecule tough ester linkages. A triglyceride ("TG") (also known as triacylglycerol or triacylglyceride) is a glyceride in which the glycerol is esterified with three fatty acids. An acyl group is a function group derived by the removal of one or more hydroxyl group and oxoacid.

Triglycerides may also be classified as having a long or medium chain length. Long chain triglycerides preferably contain fatty acids with 14 or more carbons, while medium chain triglycerides preferably contain fatty acids with 6 to 12 carbons. Long chain triglycerides may include omega- and omega-6 fatty acids. Medium chain triglycerides have saturated fatty acids and thus do not contain omega-6 or omega-3 fatty acids. Long chain triglycerides (LCT) and medium chain triglycerides (MCT) may serve as energy sources. Medium chain triglycerides may influence the metabolism of emulsion droplets because of their fast hydrolysis and other properties (i.e. enhancing particle binding to cells).

Lipolysis refers to the hydrolysis of a glyceride into glycerol and fatty acids. Lipolysis is the rate-determining step of lipid metabolism. The maximum metabolizing rate for exogenous long chain (e.g. for soybean emulsion) triglycerides is about 3.8 g of lipid/kg body weight per day (Hallberg et al., Acta Physiol. Scand. (1965) Vol. 65, Suppl. 254, page 16). Triglycerides typical of fish oils (i.e., triglycerides having a high concentration of omega-3 fatty acids e.g., higher than 30%) are hydrolyzed much more slowly than triglycerides from vegetable oils (i.e., triglycerides having predominantly fatty acids with sixteen to eighteen carbon atoms, as in soybean or olive oils), and vegetable oil long-chain triglycerides are hydrolyzed more slowly than medium chain triglycerides (MCTs). Addition of a fish oil emulsion to a long chain triglyceride (LCT) emulsion can even inhibit hydrolysis of long chain triglycerides (e.g., from soybean oil) by lipoprotein lipase (LPL).

An emulsion is a thermodynamically unstable mixture of two essentially immiscible liquids. Emulsions may typically be formed when two immiscible liquids are mechanically agitated, both phases initially tending to form droplets. When the agitation is stopped, the droplets quickly coalesce, and the two liquids separate. Usually, only one phase persists in droplet form for a prolonged period of time. This phase is called the internal (disperse or discontinuous) phase, and it is surrounded by an external (continuous) phase. The most common types of pharmaceutical or cosmetic emulsions include water as one of the phases and a lipid as the other ("the lipid phase"). If the oil or lipid droplets are dispersed in a continuous aqueous phase, the emulsion is termed oil-in-water (o/w); if the oil is the continuous phase, the emulsion is of the water-in-oil type (w/o). (Lachman et al., The Theory and Practice of Industrial Pharmacy, 3rd Ed., 1986, p. 502.)

The lifetime of the droplets is materially increased if an emulsifier is added to the two immiscible liquids. An emulsifier is a substance which stabilizes an emulsion, frequently a surfactant. Examples of food emulsifiers are egg yolk (where the main emulsifying chemical is the phospholipid lecithin), and mustard, where a variety of chemicals in the mucilage surrounding the seed hull act as emulsifiers; proteins and low-molecular weight emulsifiers are common as well. In some cases, particles can stabilize emulsions as well through a mechanism called Pickering stabilization. Both mayonnaise and hollandaise sauce are oil-in-water emulsions stabilized with egg yolk lecithin. Detergents are another class of surfactant, and will chemically interact with both oil and water, thus stabilizing the interface between oil or water droplets in suspension. This principle is exploited in soap to remove grease for the purpose of cleaning. A wide variety of emulsifiers are used in pharmacy to prepare emulsions such as creams and lotions.

Emulsions have been used as a component of parenteral nutrition to supply the body with fats in an intravenously acceptable dosage form in cases where normal (oral) nutrition is impossible, compromised or medically contraindicated or when it is necessary to promptly modify the fatty acid pattern of cells. Free fatty acids from lipid emulsions are made available to the body either when they are hydrolytically released from the infused triglycerides via the action of lipoprotein lipase (LPL) or after cellular intake of the entire emulsion particle or its remnants directly into cells.

Emulsions comprising triglycerides are known in the art. They include lipid emulsions prepared from vegetable oils (e.g., safflower or soybean oils), and, in some cases, they also contain medium chain triglycerides, long chain triglycerides and/or oils of marine origin (fish oils). Such emulsions may have a smaller weight-percentage of diglycerides and may also comprise omega-3 fatty acids. These emulsions comprise high percentages of triglycerides, which are catabolized at a slower rate than diglycerides.

Omega-3 Diglyceride Emulsions

The present invention provides a pharmaceutical composition comprising: an omega-3 diglyceride emulsion suitable for administration to a patient; and a pharmaceutically acceptable carrier, wherein the emulsion has a lipid phase of at least about 40 wt.-% of omega-3 diglycerides, and at least about 70 wt.-% of the acyl-groups of the diglycerides comprise EPA, DHA or a mixture thereof.

While not wishing to be bound by theory, it is believed that the omega-3 fatty acid content of cell membranes of certain key organs (such as the brain) and tissues can significantly be increased by administering omega-3 diglyceride containing emulsions of the present invention. Moreover, omega-3 diglyceride emulsions of the present invention will lead to a much more efficient uptake of the omega-3 fatty acid to the cell membranes than triglyceride emulsions. This is the case even when the omega-3 diglyceride emulsions of the present invention are compared to triglyceride emulsions which comprised of more rapidly-hydrolyzed glycerides such as medium-chain triglyceride or omega-6 triglycerides in vegetable oils.

While not wishing it to be bound by theory, it is believed that the omega-3 diglyceride emulsions of the present invention are advantageous over triglyceride emulsions because diglycerides are hydrolyzed faster than triglycerides, and 1,2-diglycerides are also highly bioactive molecules. Thus, omega-3 fatty acids present in the diglycerides, emulsions, are delivered to tissues rapidly while remaining (nontoxic). In addition, it is believed that diglyceride emulsion droplets are more efficiently taken up by organs than triglyceride emulsion droplets.

Diglycerides are not produced naturally in high quantities in humans, vegetables or fish. However, methods of synthesizing diglycerides are well known in the art, and are disclosed, for example, in U.S. Pat. Nos. 2,206,168; 2,626,952; 3,410,881; 3,634,473; 3,097,098; 3,551,464; 4,018,806; 5,106,542; 5,130,061; 5,142,071; 5,142,072; 5,959,128; 5,434,280; 6,004,611; 6,337,414; 6,537,787; 6,749,881; and 7,081,542 all of which are incorporated herein by reference. Thus, the diglycerides may be obtained by trans-esterification of various oils (such as fish oil or rapeseed oil) containing omega-3 unsaturated acyl-groups, and/or monoenoic acyl-groups with glycerol. Diglycerides may also be obtained by esterification of a fatty acid derived from such an oil with glycerol.

Also, esterification reactions may be performed by chemical means (such as using an alkali catalyst, i.e. sodium methoxide). Or diglycerides may be prepared by enzymatic digestion of a triglyceride with lipase to yield a 2,3-diglyceride. The resulting 2,3-diglyceride may be further processed by isomerase to yield a 1,2- or 1,3-diglyceride. Diglycerides comprising DHA and EPA may be isolated from reaction mixtures by conventional methods such as distillation or chromatography.

EPA and DHA may be obtained from any source. For example, EPA or DHA may be synthetic, isolated from natural products, or obtained from fish oil by alkaline hydrolysis. Fish oil is generally the least expensive source of EPA and DHA. Fish oils include natural fish oils, processed fish oils, highly purified fish oil concentrates or (re-)esterified (synthetic) fish oils, including (re-)esterification of omega-3-fatty acids from cold water fish oil by triglyceride hydrolysis, purification and concentration of the resultant omega-3-fatty acids with glycerol. Processed fish oils are described in European published patent application EP-A-0298293, which is incorporated herein by reference in its entirety.

Suitable exemplary fish oils include oils from cold-water fish such as salmon, sardine, mackerel, herring, anchovy, smelt and swordfish. Fish oils generally contain glycerides of fatty acids with chain lengths of 12 to 22 carbons. Highly purified fish oil concentrates obtained, for example, from sardine, salmon, herring and/or mackerel oils may have an eicosapentaenoic acid (EPA) content of from about 20 to 40 wt.-%, preferably at least about 25 wt.-%, and a docosahexaenoic acid (DHA) content of 10%, preferably at least 12%, based on the fatty acid methyl esters of the fish oil concentrate as determined by gas chromatography (percent by area). U.S. Pat. No. 6,159,523, incorporated herein by reference in its entirety, discloses a method for making fish oil concentrates. Generally, the amount of the polyunsaturated fatty acids of the omega-6 series (such as linoleic acid) in natural fish oils is low, i.e. less than 10%, preferably less than 5%.

As used herein, "wt.-%" used in conjunction with lipid phase in an emulsion refers to "g lipid per 100 mL emulsion." As used herein, "wt.-%" used in conjunction with diglyceride concentration refers to the percentage of diglyceride based on the total weight of lipid.

As used herein, "wt.-%", used in conjunction with monoglycerides of EPA/DHA or unsaturated fatty acids EPA refers to the percentage of monoglycerides of EPA/DHA or unsaturated fatty acids BPA based on the total amount of lipid.

As used herein, "wt.-%" used in conjunction with medium chain triglycerides refers to the percentage of medium chain triglycerides based on the total amount of lipid.

The present invention provides omega-3 diglyceride emulsions comprising a total lipid phase from about 7 wt.-% to about 35 wt.-%. Preferably the omega-3 diglyceride emulsions comprise a total lipid phase from about 10 wt.-% to about 20 wt.-%.

The lipid phase of the omega-3 diglyceride emulsions of the present invention preferably comprises from about 40 wt.-% to about 97 wt.-% diglycerides, based on the total weight of the lipid phase. More preferably, the lipid phase of the omega-3 diglyceride emulsions of the present invention comprise from about 60 wt.-% to about 97 wt.-% diglyceride based on the total weight of the lipid phase.

Based on the total amount of acyl groups, at least about 70 wt.-% of the acyl groups of the lipid phase comprise BPA, DH.A groups, or a mixture thereof. More preferably, about 75 wt.-% of the acyl groups of the lipid phase comprise EPA, DHA groups, or a mixture thereof. Most preferably, from about 75 wt.-% to about 90 wt.-% of acyl groups comprise BPA, DHA groups, or a mixture thereof.

The molar ratio of DHA to EPA of the acyl groups of the diglycerides in the emulsion of the present application is preferably from about 3 DHA:1 EPA to about 1DHA:1EPA. In one embodiment, the molar ratio of DHA to EPA is about 3:1. In an alternative embodiment the DHA to EPA ratio is about 1:1. For example, the molar ratio of DHA to EPA may be about 2.5:1; about 2.0:1, about 1.5:1. In other embodiments the molar ratio of DHA to EPA maybe about 1:1.5, about 1:2 about 1:2.5, or about 1:3. In yet another embodiment, at least about 70 wt.-% of the acyl groups of the diglycerides comprise either EPA or DHA only.

Omega-3 diglyceride emulsions of the present invention may further comprise from about 0 to about 60 wt.-% of monoglycerides of DHA and/or EPA. Preferably the monoglycerides of DHA and/or EPA are from about 0 wt.-% to about 10 wt.-%, more preferably from about 0 wt.-% to about 2 wt.-%, based on the total amount of lipid.

Omega-3 diglyceride emulsions of the present invention may also further comprise from about 0 to about 60 wt.-% free unsaturated fatty acids. Preferably the unsaturated fatty acids are from about 0 wt.-% to about 5 wt.-%, more preferably from about 0 wt.-% to about 2 wt.-%, based on the total amount of the lipid phase.

In one preferred embodiment of the invention, omega-3 diglyceride emulsions of the present invention comprise medium chain triglycerides (MCT) and diglycerides. Such omega-3 diglyceride emulsions may contain as a percent of total lipid from 0 to 90 wt.-% medium chain triglycerides, more preferably from about 0 wt.-% to about 60 wt.-%, most preferably from about 40 wt.-% to about 60 wt.-%. The remaining percent lipid in such emulsions preferably comprises diglycerides. Medium chain triglycerides may contain fatty acids with 6 to 12 carbons. Preferably, at least 90 wt.-% of the medium chain triglycerides are triglycerides of caprylic acid ($C_8$) and capric acid ($C_{10}$).

Omega-3 diglyceride emulsions of the invention are preferably oil-in-water (o/w) emulsions in which the dispersal phase comprises lipid and the outer continuous phase comprises distilled water purified for parenteral purposes. Such oil-in-water emulsions may be obtained by standard methods, i.e. by mixing the oil components followed by emulsification and sterilization. The pH value of omega-3 diglyceride emulsions of the present invention may be adjusted to a physiologically acceptable value, preferably to a pH of from about 6.0 to about 9.0, more preferably from about 6.5 to about 8.5. Auxiliary agents such as glycerol and additives such as antioxidants may be added to the oil mixture prior to emulsification or prior to sterilization. Omega-3 diglyceride emulsions are preferably isotonic.

Methods for making emulsions are well known in the art and are described for example in Kirk-Othmer, Encyclopedia of Chemical Technology, $3^{rd}$ Ed., v. 8, pp. 900-933 (1979). See also U.S. Pat. Nos. 2,977,283; 3,169,094; 4,101,673; 4,563,354; 4,784,845; 4,816,247, all of which are incorporated by reference in their entirety.

Omega-3 diglyceride emulsions according to the invention can be prepared by known standard procedures. Typically, first the lipids, an emulsifier and other auxiliary agents and additives are mixed first. Water is added to the mixture with dispersing. The water may optionally contain additional water-soluble components (e.g. glycerol). Energy input through shaking, stirring, homogenizers, sonication or spray processes is typically used to form the omega-3 diglyceride emulsion of the invention.

Emulsions thus obtained preferably contain lipid drops having a diameter of about 10 lam. Average droplet sizes of emulsions may be further reduced by additional homogenization, preferably by using a high-pressure homogenizer. Lipid droplets of the present invention preferably have a median particle size of less than 1 μm. For parenteral application, median lipid droplet sizes may be less than about 1 μm and preferably in the range from about 100-500 nm, more preferably from about 100 nm to about 400 nm, most preferably from about 200 nm to about 350 nm. For other applications, such as transdermal applications, mean diameter of the lipid droplet can be larger, for example, from about 1 μm and 5 μm.

Method of Treatment Using Omega-3 Diglyceride Emulsions

The present invention also provides a method for preventing organ death or injury comprising: administering to a patient a therapeutically effective amount of a pharmaceutical composition which comprise an omega-3 diglyceride emulsion suitable for administration to a patient; and a pharmaceutically acceptable carrier, wherein the emulsion comprises at least about 40 wt.-% of omega-3 diglycerides. Preferably, at least about 70 wt.-% of the acyl-groups of the diglycerides comprise of EPA, DHA or a mixture thereof.

The present invention further provides a method for reducing adverse cytokine production comprising administering to a patient in need thereof a therapeutically effective amount of a pharmaceutical composition comprising: an omega-3 diglyceride emulsion suitable for administration to a patient; and a pharmaceutically acceptable carrier, wherein the emulsion comprises at least about 40 wt.-% of omega-3 diglycerides. Preferably, at least about 70 wt.-% of the acyl-groups of the diglycerides comprise of EPA, DHA or a mixture thereof.

While not wishing to be bound by theory, it is believed that omega-3 fatty acids present in the emulsion decrease pro-inflammatory cytokine production by suppressing production of agents (such as TNF-alpha) that facilitate tissue breakdown. High cytokine concentrations are believed to impair hydrolysis of circulating glycerides by lipoprotein lipase (LPL).

The present invention further provides a method for reducing cell death or damage resulting from hypoxia-ischemia comprising administering to a patient in need thereof a therapeutically effective amount of a pharmaceutical composition comprising: an omega-3 diglyceride emulsion suitable for administration to a patient; and a pharmaceutically acceptable carrier, wherein the emulsion comprises at least about 40 wt.-% of omega-3 diglycerides. Preferably, at least about 70 wt.-% of the acyl-groups of the diglycerides comprise of EPA, DHA or a mixture thereof.

Hypoxia refers to a shortage of oxygen in the body. Ischemia refers to insufficient blood flow to provide adequate oxygenation. The most common causes of ischemia are acute arterial thrombus formation, chronic narrowing (stenosis) of a supply artery that is often caused by atherosclerotic disease, and arterial vasospasm. As blood flow is reduced to an organ, oxygen extraction increases. When the tissue is unable to extract adequate oxygen, the partial pressure of oxygen within the tissue fails (hypoxia) leading to a reduction in mitochondrial respiration and oxidative metabolism. Further, in many acute situations of organ ischemia-hypoxia (e.g., stroke, myocardial infarction, intestinal volvulus, etc.) the patient is far too ill to have oral or enteral administration of therapeutic agents and thus needs parenteral injections, such as from lipid emulsions for immediate action.

While not wishing it to be bound by theory, it is believed that organ death or injury, is frequently precipitated by hypoxia-ischemia, or associated with hypoxia-reperfusion damage, cardiac arrhythmias, organ transplantation, endothelial dysfunction, impaired organ micro perfusion, increased risk of thrombus formation, or ectopic fat deposition, etc. Ectopic fat depositions usually occur in organs not specialized in fat deposition, such as liver, pancreas, or heart.

The present invention also provides a method of limiting neurological damage resulting from hypoxia-ischemia comprising, administering an omega-3 diglyceride lipid emulsion after a cerebral hypoxia-ischemia insult wherein the omega-3 diglyceride lipid emulsion comprises at least about 40 wt.-% of a diglyceride. Preferably, at least about 70 wt.-% of the acyl-groups of said diglycerides comprise EPA and DHA groups.

The methods of the present invention are believed to be able to prevent organ death or injury when hypoxia-ischemia and/or its sequelae has occurred or is going to occur in the organs selected from the group comprising brain, lung, heart, kidney, spinal cord, lower or upper limbs, and large or small intestine.

In another embodiment of the invention, methods preventing organ, death or injury, or limiting/preventing cell death and cell/tissue damage resulting from hypoxia-ischemia and or its sequelae comprise administering an omega-3 diglyceride lipid emulsion of the present invention in conjunction with standard available therapies (such as surgery and angioplasty) and/or medications given to prevent or treat hypoxia-ischemia. For example, the following drugs may be administered with the omega-3 diglyceride emulsion: antiplatelet medications such as aspirin, clopidogrel, dipyridamole, ticlopidine; anticoagulants (problems of increasing hydrolysis and FFA release); and thrombolytic agents such as tissue plasminogen activator.

Omega-3 diglyceride emulsions according to the present invention may be used to treat patients with a global omega-3 fatty acid deficiency or a relative deficiency in cell membranes of certain organs or tissues, including heart, brain, kidney, lung, liver, pancreas, adipose tissue, endothelium, white blood cells, platelets and immune cells, or those patients with a condition benefiting from increasing availability of omega-3 fatty acids. Emulsions and methods of the present invention may be used for the treatment of surgical or percutaneous revascularization, such as in coronary or other "peripheral" arteries, myocardial schemia or infarction, unstable angina, transient cerebral ischemia or stroke, inflammation, auto-immune and thrombotic diseases, such as venous or arterial diseases, organ transplantation (with infusion in both donors and recipients), abdominal operations, multiple trauma, infections, impending or manifest sepsis, cachexia (wasting) diseases, angiographic procedures, pre-term infants (especially for raising the omega-3 fatty acid content in the brain and retina), excessive acute phase reactions, acute respiratory distress syndrome, intestinal ischemia, cardiovascular complications of diabetes mellitus, severe burns, Raynaud's disease, conditions of ectopic fat deposition (e.g., hepatic steatosis) and omega-3 fatty acid deficiency in cell membranes or patients unable to absorb large amounts of omega-3 fatty acids. Omega-3 diglyceride emulsions according to the invention can also be used for administration in patients with impaired tissue or organ perfusion, increased risk of severe cardiac arrhythmia (e.g. ventricular fibrillation), or during dialysis in patients treated with haemodialysis. The invention may be administered for pre-operative conditions or post-operative conditions or in severe or persistent post-aggression metabolic response following operations. Omega-3 diglyceride emulsions of the invention may also be used in the manufacture of medicaments or pharmaceutical compositions for the treatment of the above-mentioned diseases.

Administration of the omega-3 diglyceride lipid-based emulsion may be either enteral, parenteral, or transdermal. The methods of administration a pharmaceutical composition of omega-3 diglyceride in the present invention may further comprise any additional administrations of other conventional stroke treatment or preventative medication.

Omega-3 diglyceride lipid-based emulsions may be administered at any effective dose, and may be administered any time after an organ injury, or a hypoxia-ischemia insult, or operation, such as 5 to 20 minutes to six hours after the injury, insult, or operation; or 0-12 hours after the injury, insult, or operation. Additional later administrations are also contemplated, for example, an additional later administration is provided 1-24 hours after the injury, insult, or operation. The Omega-3 diglyceride lipid based emulsions may also be administered at any effective dose, before the injury, insult, or operation, such as 1 hour prior to the injury, insult, or operation.

Omega-3 diglyceride emulsions of the invention may contain from about 2 wt.-% to about 5 wt.-% of a stabilizing or isotonizing additive, such as a polyhydric alcohol, based on the emulsion. Preferred stabilizing or isotonizing additives include glycerol, sorbitol, xylitol or glucose. Glycerol is most preferred.

In addition to distilled water, omega-3 diglyceride emulsions may contain conventional auxiliary agents and/or additives, such as emulsifiers, emulsifying aids (co-emulsifiers), stabilizers, antioxidants, and isotonizing additives.

Emulsifiers may include physiologically acceptable emulsifiers (surfactants) such as phospholipids of animal or vegetable origin. Examples of phospholipids are egg yolk lecithin, a biologic phospholipid, a phosphatidylcholine with fixed fatty acyl chain composition, a glycophospholipid or a phosphatidylethanolamine. Particularly preferred are purified lecithins, especially soybean lecithin, egg lecithin, or fractions thereof, or the corresponding phosphatides. The emulsifier content may vary from about 0.02.wt.-% to about 2.5 wt.-%, preferably from about 0.6 wt.-% to about 1.5 wt.-% and most preferably about 1.2 wt.-%, based on the total emulsion. In one embodiment the emulsifier is 1.2 mg of egg yolk lecithin/100 ml emulsion.

Alkali metal salts, preferably sodium salts, of long chain, $C_{16}$ to $C_{28}$ fatty acids may also be used as emulsifying aids (co-emulsifiers). The co-emulsifiers are employed in concentrations of from about 0.005 wt.-% to about 0.1 wt.-%, preferably about 0.02 wt.-% to about 0.04 wt.-%, based on the total emulsion. Further, cholesterol or a cholesterol ester alone or in combination with other co-emulsifiers may be employed as an emulsifying aid in a concentration of from about 0.005 wt.-% to about 0.1 wt.-%, preferably from about 0.02 wt.-% to about 0.04 wt.-%, based on the emulsion.

Omega-3 diglyceride emulsions may further comprise an effective amount of an antioxidant, such as vitamin E, in particular α-tocopherol (the most active isomer of vitamin E in humans) as well as β- and γ-tocopherol, and/or ascorbyl palmitate as antioxidants and thus for protection from peroxide formation. The total amount of alpha tocopherol may be up to 5000 mg per liter. In a preferred embodiment the total amount of said antioxidant is from about 10 mg to about 2000 mg, more preferably from about 25 mg to about 1000 mg, most preferably from about 100 mg to 500 mg, based on 100 g of lipid.

Omega-3 diglyceride emulsions of the invention may be administered orally, enterally, parenterally, transdermally, intravascular, intravenatin, intramusala, intraperitoneal or transmucosally, and are preferably administered by intravenous injection. Thus the present invention also relates to a pharmaceutical composition comprising omega-3 diglyceride emulsions as described herein, preferably for injection into the human or animal body.

Pharmaceutical compositions of the invention may further comprise various pharmaceutically active ingredients. In particular, the pharmaceutically active ingredient may be delivered to a particular tissue of the body (drug targeting) in combination with emulsions of the present invention. Omega-3 diglyceride emulsions may include carriers for such targeted tissue treatment. Suitable carriers may be, for example, macromolecules linked to the emulsion droplet, lipid microspheres comprising soybean oil or lecithin or fish oil U.S. Pub. No. 2002/0155161, incorporated herein by reference in its entirety, discloses tissue-targeted delivery of emulsions.

The pharmaceutical composition may be formulated into a solid or a liquid dosage form. Solid dosage forms include, but are not limited to, tablets, pills, powders, granules, capsules, suppositories, and the like. Liquid dosage forms include, but are not limited to liquids, suspensions, emulsions, injection preparations (solutions and suspensions), and the like. The choice of dosage form may depend, for example, on the age, sex, and symptoms of the patient.

The pharmaceutical composition may optionally contain other forms of omega-3 diglyceride emulsions and/or additional active ingredients. The amount of omega-3 diglyceride emulsions or other active ingredient present in the pharmaceutical composition should be sufficient to treat, ameliorate, or reduce the target condition.

The pharmaceutically acceptable excipient may be any excipient commonly known to one of skill in the art to be suitable for use in pharmaceutical compositions. Pharmaceutically acceptable excipients include, but are not limited to, diluents, carriers, fillers, bulking agents, binders, disintegrants, disintegration inhibitors, absorption accelerators, wetting agents, lubricants, glidants, surface active agents, flavoring agents, and the like.

Carriers for use in the pharmaceutical compositions may include, but are not limited to, lactose, white sugar, sodium chloride, glucose, urea, starch, calcium carbonate, kaolin, crystalline cellulose, or silicic acid.

Absorption accelerators may include, but are not limited to, quaternary ammonium base, sodium laurylsulfate, and the like.

Wetting agents may include, but are not limited to, glycerin, starch, and the like. Adsorbing agents used include, but are not limited to, starch, lactose, kaolin, bentonite, colloidal silicic acid, and the like.

In liquid pharmaceutical compositions of the present invention, the omega-3 diglyceride emulsions of the present invention and any other solid ingredients are dissolved or suspended in a liquid carrier, such as water, vegetable oil, alcohol, polyethylene glycol, propylene glycol or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention can also contain viscosity enhancing agents to improve the mouth-feel of the product and/or coat the lining of the gastrointestinal tract. Such agents include for example acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar can be added to improve the taste. Preservatives and chelating agents such as alcohol, sodium benzoate, butylated hydroxy toluene, butylated hydroxyanisole and ethylenediamine tetraacetic acid can be added at safe levels to improve storage stability.

A liquid composition according to the present invention can also contain a buffer such as guconic acid, lactic acid, citric acid or acetic acid, sodium guconate, sodium lactate, sodium citrate or sodium acetate.

Selection of excipients and the amounts to use can be readily determined by an experienced formulation scientist in view of standard procedures and reference works known in the art.

When preparing injectable pharmaceutical compositions, solutions and suspensions are sterilized and are preferably made isotonic to blood. Injection preparations may use carriers commonly known in the art. For example, carriers for injectable preparations include, but are not limited to, water, ethyl alcohol, propylene glycol, ethoxylated isostearyl alcohol, polyoxylated isostearyl alcohol, and fatty acid esters of polyoxyethylene sorbitan. One of ordinary skill in the art can easily determine with little or no experimentation the amount of sodium chloride, glucose, or glycerin necessary to make the injectable preparation isotonic. Additional ingredients, such as dissolving agents, buffer agents, and analgesic agents may be added. If necessary, coloring agents, preservatives, perfumes, seasoning agents, sweetening agents, and other medicines may also be added to the desired preparations.

Pharmaceutical compositions of the invention may further comprise various pharmaceutically active ingredients. In particular, the pharmaceutically active ingredient may be delivered to a particular tissue of the body (drug targeting) in combination with micro emulsions of the present invention. Omega-3 diglyceride emulsions may include carriers for such targeted tissue treatment. Suitable carriers may be, for example, macromolecules linked to the emulsion droplet, lipid microspheres comprising soybean oil or lecithin or fish oil. U.S. Pub. No. 2002/0155161, incorporated herein by reference in its entirety, discloses tissue-targeted delivery of emulsions.

Omega-3 diglyceride compositions of the invention allow for rapid and efficient uptake of omega-3 fatty acids, including BPA and DHA, into cell membranes of organs and tissues. Accordingly, there is provided a method for delivering an emulsion of omega-3 diglycerides enriched with EPA and DHA to cells and organs by administering omega-3 diglyceride emulsions of the present invention.

Lipolysis of emulsions of the invention facilitates the release of free omega-3 fatty acids and monoglycerides into the bloodstream or in cells. Free fatty acids may be transported into mitochondria for use as an energy source, or may be incorporated into cell membranes. Enriching cell membranes and phospholipids with omega-3 long chain polyunsaturated fatty acids (PUPA) may help promote or restore an adequate balance between omega-3 and omega-6 fatty acids. Incorporation of EPA and DHA also increases membrane fluidity and flexibility.

The invention includes methods of treatment using omega-3 diglyceride emulsions of the present invention. The present invention also provides means of preventing or reducing organ lipid excess deposition and/or cell and/or organ damage/death due to hypoxia-ischemia by administering an omega-3 diglyceride lipid emulsion of the present invention. Thus, there is generally an increase in free fatty acid concentration following an ischemic event, which inhibits mitochondrial respiratory functions and leads to cell death. In the brain, for example, it is necessary to repair cell membranes because normal membranes are necessary for proper structure and function of synaptic membranes.

Fatty acids present in the omega-3 lipid emulsion of the present invention may be used as an energy source or incorporated into cell membranes. Omega-3 diglyceride emulsions of the present invention may be used to reduce or prevent cell damage/death in any organ that may be affected by ischemia, including but not limited to the brain, heart, kidney, lung and intestine. Preferably the emulsions are administered either enterally (for example, orogastric or nasogastric) or parenterally (for example, subcutaneous, intravenous, intramuscular, intraperitoneal, transdermal and transmucosal are considered parenterally). Most preferably the emulsion is administered intravenously.

Omega-3 diglyceride emulsions of the present invention are preferably provided at a dose effective for the respective treatment. For example, there is evidence that DHA and EPA are involved in cell signaling that promotes survival of certain cell types. N. G. Bazan, *Trends Neurosci.*, 29(5):263-71 (2006); Lukiw, et al., *J. Clin. Invest.*, 115(10): 2774-83 (2005); N. G. Bazan, *Mol. Neurobiol.*, 31(1-3): 219-30 (2005). Those skilled in the art would be able to determine the appropriate dose based on the experimental data presented herein. However, for example a suitable effective and tolerable dose for a human would be about 0.05 g/kg to 4.0 g/kg per day, preferably about 0.3 g to about 1.5 g glyceride per kg body weight per day. Higher doses may be given as necessary. Administration may be continuous or in the form of one or several doses per day. One skilled in the art would appreciate appropriate dosage and routes of administration based upon the particular subject and condition to be treated.

Omega-3 diglyceride emulsions of the present invention are preferably administered parenterally and/or enterally after the ischemic insult (or in some embodiments, before the insult when it can be anticipated). The emulsion may be administered to prevent/reduce tissue damage after cerebral hypoxia or stroke as well as hypoxic-ischemic insults in other organs such as heart, kidney, lung, etc. Preferably omega-3 diglyceride emulsions of the present invention are administered as soon as possible after the insult (or before in cases where the insult can be predicted) to provide for a greater reduction of cell death. For example, in a preferred embodiment an omega-3 diglyceride lipid emulsion of the present invention is administered from 0-12 hours after the insult. Ideally the administration occurs anywhere from 20 minutes to 6 hours after the insult. Most preferably the emulsion is administered 0-2 hours after the insult. The present invention also provides for multiple administrations of omega-3 diglyceride emulsions of the present invention. For example, the emulsion may be first administered before or within 20 minutes of the insult, followed by a second administration 1-24 hours after the insult. The present invention also contemplates multiple administration(s) of omega-3 diglyceride emulsions following the insult.

The foregoing description has been directed to particular embodiments of the invention for the purposes of illustration and explanation. It will be apparent to those skilled in the art, however, that modifications, changes and variations may be applied to the present invention without departing from the scope and spirit of the claimed invention. It is intended that the following claims be interpreted to embrace all such modifications and changes.

EXAMPLES

Example 1

Method of Preparation of Diglyceride Emulsions

DG Lipid Emulsions. Phospholipid-stabilized emulsions of n-3 DG (20 g of DG/100 ml) are prepared with fish oil DG, respectively, and egg yolk phospholipid.

Each emulsion contains 20 g of DG, which is emulsified by 1.2 g of egg yolk lecithin, and 2.5 g of glycerol/100 mL. The emulsion lipids are mixed in doubly distilled water (30 g of water and 20 g of oil) and dispersed by means of an Ultra-Turrax (Janke and Kunkel KG, Staufen, West Germany) for 10 min; water is added to give a final volume of 100 mL, and emulsions are dispersed for an additional 10 min. Subsequently, the dispersion is homogenized by ultrasound in a cooling cell with a Labsonic 2000 homogenizer for 10 min at an energy input of 200 W. The emulsions are then sealed in 5 mL vials under N2, and thereafter kept at 4° C. Mean particle sizes are determined by laser spectroscopy, and both are similar in size and homogeneity with mean diameters between 290 and 300 nm. N-3 DG emulsion contains 1.42±0.25 (mean±standard deviation for three measurements) of total DG as FFA, i.e., a range of 0.0006-0.0009 mM, concentrations too low to significantly affect emulsion metabolism.

Example 2

60 Minutes of Hypoxia-Ischemia

Postnatal day 19-21 Wistar rats of both genders are subjected to unilateral (right) carotid artery ligation. See Rice, J. E., 3rd, R. C. Vannucci, et al. (1981), "The influence of immaturity on hypoxic-ischemic brain damage in the rat," Ann Neurol 9(2): 131-41 and Vannucci, S. J., L. B. Seaman, et aL (1996), "Effects of hypoxia-ischemia on GLUT1 and GLUT3 glucose transporters in immature rat brain," Journal of Cerebral Blood Flow & Metabolism 16(1): 77-81.

Immediately after ligation, six rats are given 50 mg 20% diglyceride omega-3 lipid-based emulsion (0.25 cc)(a 20% long chain omega-3 diglyceride-based formula having ≥70% of total omega-3 diglyceride fatty acid as eicosapentaenoic acid (EPA) and docosahexaenoic acid (DHA)) via orogastric feeding tube, and six control rats are given 0.25 cc water, both enterally. The 20% omega-3 diglyceride lipid-based emulsion is made placing 20 g of omega-3 diglyceride in 100 ml of water, and emulsifying with 1.2 g of egg yolk lecithin. Rats are allowed to recover for 2 hours, then they undergo hypoxia-ischemia for 60 minutes of 8% oxygen at a constant temperature. The six pre-treated rats are given another dose of 50 mg omega-3 diglyceride lipid-based emulsion immediately after the hypoxia-ischemia and control rats are given another 0.25 cc water. All rats are euthanized at 72 hours of reperfusion. The brains are removed and cut into 2 mm sections and stained with 2,3,5, Triphenyl-2H-tetrazolium chloride (TTC). TTC is a vital die that stains cells red that have respiring mitochondria. Dead tissue (infarct) appears white.

The sections are scored as follows:
0—no evidence of edema or cell death
1—edema without cell death
2—edema with minimal cell death
3—edema with significant cell death All rats survive 60 minutes of hypoxia-ischemia. Six of the six control rats have edema and/or cell death with a mean score of about 2.0, while two of the six treated rats are expected to have a mean score of 0.3.

Example 3

65 Minutes of Hypoxia-Ischemia

Postnatal day 19-21 Wistar rats of both genders are subjected to unilateral (right) carotid artery ligation. Immediately after ligation, six rats are given 50 mg 20% omega-3 diglyceride lipid-based emulsion (0.25 cc)(20% omega-3 diglyceride fatty acid based formula having ≥70% of total omega-3 diglyceride fatty acid as EPA and DHA)) via orogastric feeding tube and six control rats are given 0.25 cc water, both enterally. The emulsion is made as described in Example 1. The rats are allowed to recover for two hours, and then undergo hypoxia-ischemia for 65 minutes of 8% oxygen at a constant temperature. The six pre-treated rats are given another dose of 50 mg omega-3 diglyceride lipid-based emulsion immediately after the hypoxia-ischemia and control rats are given another 0.25 cc water. All rats are euthanized at 72 hours of reperfusion. The brains are removed and cut into 2 mm sections and stained with 2,3,5, Triphenyl-2H-tetrazolium chloride (TTC).

The sections are scored as follows:
0—no evidence of edema or cell death
1—edema without cell death
2—edema with minimal cell death
3—edema with significant cell death The 65 minutes of hypoxia-ischemia produce damage in all rats. Four of the six control rats survive with a mean score of around 2.5, while five of the six treated rats are expected to survive with a mean score of 1.5.

Example 4

Treatment of Rats with Omega-3 Diglyceride Lipid Emulsion Prior to 60 Minutes of Hypoxia Postnatal day 19-21 Wistar rats are subjected to unilateral (right) carotid artery. Immediately after ligation, six rats are given 50 mg of a 20% omega-3 diglyceride lipid-based emulsion (0.25 cc), and six control rats are given 0.25 cc water, both enterally. The emulsion is as described above in Example 1. Rats are allowed to recover for two hours, then undergo hypoxia-ischemia for 60 minutes of 8% oxygen at a constant temperature. The six pre-treated rats are given another dose of 50 mg omega-3 diglyceride lipid emulsion immediately after the hypoxia/ischemia and control rats are given another 0.25 cc water. At 72 hours of reperfusion, the rats are euthanized and their brains are removed, cut into 2 mm sections and stained with 2,3,5 triphenyl-2H-tetrazolium chloride (TTC). The damage in each animal is then given a score from 0 (no damage) to 4 (>60% ipsilateral hemisphere infarcted). All of the vehicle-treated animals suffer brain damage, with a mean damage score of about 2.00; the omega-3 diglyceride lipid emulsion-treated rats are expected to be significantly less damaged, having a mean damage score 0.3.

The results are expected to show that when omega-3 diglycerides are administered either immediately before and/or after hypoxia-ischemia the animals confer a significant neuroprotection. Superior results are expected to be obtained when the omega-3 diglyceride are injected parenterally.

Example 5

Treatment Following Hypoxia-Ischemia

Post-natal day 19-21 rat pups are subjected to unilateral carotid artery litigation and 60 minutes of hypoxia-ischemia, according to the previously described protocol. On four separate occasions, rats are treated by parenteral injection of omega-3 diglyceride lipid-based emulsion (100 mg) immediately after the insult, and again at four hours after the insult. The emulsion is as described above in Example 1. Brain damage is evaluated by TTC staining at 72 hours of reperfusion. In each instance, administration of the omega-3 diglyceride lipid-based oil emulsion provides greater than 50% protection, i.e. reduction of tissue damage.

The results of these experiments are expected to represent the significance of the overall protection. It is expected that 50% of the treated animals are 100% protected (no damage at all, compared to 1/14 untreated; 40% suffered only mild damage, compared to 1/14 mildly damaged untreated animals). The results are expected to indicate that treatment following hypoxia-ischemia provides a neuroprotective benefit as indicated by a reduction of tissue damage.

Example 6

Quantification of Effects of Omega-3 Diglyceride Treatment on Cellular Targets

Studies on the effects of omega-3 diglyceride treatment on the generation of reactive oxygen species (ROS) and markers of oxidative damage, as well as indices of inflammation at 2, 4, 8 and 24 h after the hypoxic/ischemic insult are performed. Lasting protection is expected to confirm by brain histopathology at eight weeks following the original hypoxia-ischemic. Sections of the brain are stained (including both involved and non-involved hemispheres) with antibodies recognizing activated proteins known to participate in neuronal apoptosis (caspase 3, Jun N-terminal kinases), neuronal survival (activated Akt, phosphorylated BAD, FKHR) or to mediate the effects of NMDA-R signaling (CAM KII, and protein kinase C isoforms, in particular PKCγ and PKCЄ). Sections are co-stained with antibodies recognizing neuronal specific proteins (Tau), astrocytes (GFAP) or microglia. These analyses will allow quantification of the effect of omega-3 diglyceride on hypoxia-ischemia induced changes in apoptotic versus anti-apoptotic signaling in neurons, as well as gain indices of astrocytic or microglia involvement. Further, whole brain extracts from involved and non-involved hemispheres are prepared to quantify the extent of caspase, JNK and Akt activation by immunoblotting. These extracts are also used to address the question of whether omega-3 diglycerides treatment effects the activation of brain sterol regulatory element binding proteins (SREBP) in vivo.

What is claimed is:

1. An omega-3 lipid-based oil-in-water emulsion suitable for administration to a subject, wherein
    (a) the emulsion comprises at least about 7% to about 35% omega-3 oil by weight in grams per 100 ml of emulsion,
    (b) the omega 3 oil comprises at least about 40%-to about 97% omega-3 diglyceride by weight per total weight of the omega-3 oil, and at least about 70 wt.-% of the acyl-groups of the omega-3 diglycerides comprise EPA, DHA or a mixture thereof,
    (c) the omega-3 oil comprises less than about 10% omega 6 fatty acids, and
    (d) the mean diameter of lipid droplets in the emulsion is less than about 1 micron.

2. The omega-3 diglyceride emulsion of claim 1, wherein lipid droplets of the emulsion have a medium particle size of about 100 to 500 nm.

3. The emulsion of claim 1, wherein the total DHA and EPA content of the omega-3 oil are present in a molar ratio of from about 3:1 to about 1:1.

4. The emulsion of claim 1, wherein at least about 75 wt.-% of the acyl-groups of the diglycerides comprise EPA, DHA or a mixture thereof.

5. The emulsion of claim 1, wherein at least from about 75% to about 90% of the acyl-groups of the omega-3 diglycerides comprise EPA, DHA or a mixture thereof.

6. A method for reducing cell death or cell damage, comprising administering to a subject in need thereof a therapeutically effective amount of a pharmaceutical composition comprising the emulsion of claim 1.

7. The method of claim 6, wherein the cell death or cell damage results from hypoxia-ischemia, organ transplantation, or cardiac arrhythmia.

8. The method of claim 6, wherein the cell death or cell damage occurs in an organ selected from the group consisting of brain, heart, kidney, spinal cord, large or small intestine, lung, liver, and pancreas.

9. A method comprising:
 (a) identifying a subject who has undergone hypoxia-ischemia,
 (b) administering to the subject a therapeutically effective amount of the omega-3 lipid-based oil-in-water emulsion of claim 1 after the hypoxia-ischemia insult to reduce hypoxia-reperfusion damage in liver or pancreas.

* * * * *